Jan. 29, 1974 H. B. WHITMORE Plant Pat. 3,456
RHUBARB PLANT
Filed April 25, 1972
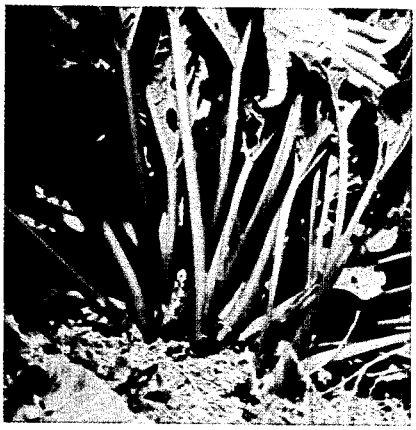

United States Patent Office

Plant Pat. 3,456
Patented Jan. 29, 1974

3,456
RHUBARB PLANT

Harold B. Whitmore, 223 Walnut Lane NW., Vienna, Va. 22180

Filed Apr. 25, 1972, Ser. No. 247,340
Int. Cl. A01h 5/00
U.S. Cl. Plt.—89 1 Claim The present invention comprises a new and distinct variety of rhubarb plant botanically classified as *Rheum rhaponticum* and known by the varietal name Whitmore red. The new plant was discovered by me as a single plant in a cultivated area in Vienna, Va., and has been continuously asexually reproduced in Vienna, Va., and elsewhere by dividing the crows formed during the preceding season.

Rhubarb of the garden type to which the present invention relates is a perennial vegetable grown primarily for its edible leaf stalks which vary in taste from strongly to mildly tart, and in color from green, through pink, to deep red depending upon the variety. Popular varieties in the United States are Canada Red, McDonald and Valentine, all of which are red-stalked varieties having a relatively less tart or sweeter taste.

The red-stalked varieties due to this sweeter taste are generally the most popular, but, unfortunately, have rarely been successfully grown in the southern part of the United States due to climate and soil conditions. The relatively higher heat and humidity and the generally heavy clay soils found in the South make the red-stalked varieties of rhubarb particularly susceptible to a disease commonly known as "foot rot," which is generally considered to be the most serious disease affecting rhubarb growth. Such disease destroys rather quickly the roots of the plant, and as a result it is common in the South for the red-stalked varieties of rhubarb to fail to thrive, or even to survive, more than a few months. Such was my experience with all of the red-stalked varieties commercially obtained, when planted in Vienna, Va.

As mentioned briefly above, the new variety was discovered by me as a single plant in a cultivated area in Vienna, Va., which was being prepared for planting. Although I did not expect the plant to survive for long for the reasons above mentioned, the plant was protected and nourished, and survived the entire season. The stalk growth was abundant, with the stalks severed for eating purposes displaying an excellent sweetness of taste. The variety was asexually reproduced that year and each year thereafter by crown division, and has been found to retain its distinctive characteristics through successive propagations. In order to establish growth of the new variety under different soil and climatic conditions in generally the same geographical area, the variety has also been grown in the eastern shore of southern Maryland, and has flourished abundantly.

In addition to this outstanding and unique disease resistant feature which now makes possible abundant and flourishing growth in relatively hot southern climes, the new variety is characterized by excellent taste and sweetness, and an unusually long harvesting season. The new variety tastes even somewhat sweeter than other red varieties, and is much sweeter than Victoria, a well-known commercial variety with pink stalks, or other pink-stalked plants. In preparing the stalks for eating, less sugar is required to produce a pleasantly sweet but yet tart taste. The new variety also is characterized by essentially no stringiness in the stalks, an undesirable feature which detracts from certain presently available varieties.

Another most surprising characteristic of the new variety is the exceptional continuing season-long harvest, with the plant continuously developing succulent new stalks which may be removed from the plant repeatedly from spring until frost. This characteristic makes the new variety ideal for home garden use. The new variety does not develop dry and hollow stalks late in the growing seasons as is often the case with prior rhubarb varieties, whereby an essentially uninterrupted harvest occurs until frost.

A further advantageous characteristic of the new variety is its rapid and abundant growth which makes it possible to partially harvest the stalks during the second year of growth without damaging the plant. By way of comparison, it is advisable with most commercially available red rhubarb varieties to wait until the third year of growth before even partially harvesting the stalks.

The new variety is illustrated in the accompanying drawing which comprises a color photograph of the new variety. The leaves of the new variety are not distinctive, being similar in shape and green color to the leaves of known varieties. The coloring of the leaves changes little as the plant matures. The red stalk color is representative in color of the relatively sweet tasting varieties presently on the market which have been, almost without exception, unable to flourish in the southern climes. The characteristic of abundant stalk production will be noted.

The plant illustrated in the application drawing is between two and three years old, with the plant being transplanted, however, about 6 months prior to the time the picture was taken. As a result, the stalks are somewhat shorter in length than would normally be the case for mature plants of that age. The stalk length for mature plants is up to two feet, measured from the top of the crown to the leaf. As far as known, the stalk length and diameter is not distinctive, with the stalk diameter varying from approximately ¾" for immature stalks to 1¼" for mature stalks.

I claim:

1. A new and distinct variety of rhubarb plant of the type having relatively red stalks, particularly characterized by its unique disease-resistant ability to flourish in relatively southern climes; its relatively sweet taste; its rapid growth habit, and its continuous season-long harvest which permits succulent edible new stalks to be harvested continuously from spring until frost.

No references cited.

ROBERT E. BAGWILL, Primary Examiner